(12) United States Patent
Kwon et al.

(10) Patent No.: US 11,026,633 B2
(45) Date of Patent: Jun. 8, 2021

(54) METHOD FOR DETECTING MOTION ARTIFACT USING WAVELET TRANSFORM

(71) Applicant: UNIVERSITY OF ULSAN FOUNDATION FOR INDUSTRY COOPERATION, Ulsan (KR)

(72) Inventors: Sungoh Kwon, Ulsan (KR); Da Hee Ban, Ulsan (KR)

(73) Assignee: UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 503 days.

(21) Appl. No.: 15/741,493

(22) PCT Filed: Dec. 30, 2015

(86) PCT No.: PCT/KR2015/014533
§ 371 (c)(1),
(2) Date: Jun. 4, 2018

(87) PCT Pub. No.: WO2017/007098
PCT Pub. Date: Jan. 12, 2017

(65) Prior Publication Data
US 2018/0263566 A1    Sep. 20, 2018

(30) Foreign Application Priority Data

Jul. 3, 2015    (KR) .................. 10-2015-0095577
Dec. 22, 2015    (KR) .................. 10-2015-0183789

(51) Int. Cl.
*H03F 1/26*    (2006.01)
*A61B 5/00*    (2006.01)
*A61B 5/024*    (2006.01)

(52) U.S. Cl.
CPC .......... *A61B 5/726* (2013.01); *A61B 5/02416* (2013.01); *A61B 5/7207* (2013.01); *A61B 5/725* (2013.01); *A61B 5/7246* (2013.01)

(58) Field of Classification Search
CPC ...................................................... A61B 5/726
USPC ...................................................... 702/191
See application file for complete search history.

(56) References Cited

U.S. PATENT DOCUMENTS

| | | | |
|---|---|---|---|
| 8,700,111 B2* | 4/2014 | LeBoeuf | A61B 5/002 600/310 |
| 10,278,647 B2* | 5/2019 | Salehizadeh | A61B 5/0245 |
| 2009/0105556 A1* | 4/2009 | Fricke | A61B 5/0205 600/301 |

* cited by examiner

*Primary Examiner* — Aditya S Bhat
(74) *Attorney, Agent, or Firm* — Womble Bond Dickinson (US) LLP (57) ABSTRACT

A motion artifact detecting method using wavelet transform which is capable of removing the problem caused by a radio noise and a motion artifact generated during the measurement of a PPG signal which is one of bio-signals, the method including: measuring a PPG signal; generating a signal obtained by removing a radio noise from the measured PPG signal; setting a reference signal from the signal from which the radio noise is removed; selecting a base signal based on the set reference signal; performing wavelet transform using the base signal; and detecting and removing a motion artifact using the wavelet-transformed value.

6 Claims, 9 Drawing Sheets

METHOD FOR DETECTING MOTION ARTIFACT USING WAVELET TRANSFORM

RELATED APPLICATION

The present application is a national stage application of International Patent Application No. PCT/KR2015/01453312 filed on Dec. 30, 2015, which claims the benefit of priority from Korean Patent Application No. 10-2015-0095577 filed on Jul. 3, 2015 and Korean Patent Application No. 10-2015-0183789 filed on Dec. 22, 2015, the entire disclosure of which is incorporated herein by reference.

BACKGROUND

Technical Field

The present invention relates to a motion artifact detecting method using wavelet transform, and more particularly, to a motion artifact detecting method using wavelet transform which determines whether a motion artifact is included in a PPG signal which is one of bio-signals by receiving and time-synchronizing multiple signals to remove the motion artifact.

Background

Recently, as the incidence of various diseases has increased, there has been an increasing interest of modern people in the health and ways of preventing various diseases. Many medical devices that determine the presence or absence of a disease in the body and treat the disease are also developed to identify the disease by a simple method. However, the disease needs to be examined using the above-mentioned method directly at the hospital, and the members of society seek a way to check their body condition in real time instead of going to the hospital. Therefore, recently, researches on Ubiquitous technology which provides medical services without restriction of time and space and U-healthcare technology which remotely utilizes the technology have been actively carried out.

There are various types of measurable bio-signals including electroencephalography (EEG), electrocardiography (ECG), electromyography (EMG), photoplethysmography (PPG), and electrooculography (EOG), and the like.

When various bio-signals are treated, the PPG is a signal which can be simply measured and monitored. EEG and ECG need to be measured by attaching an electrode to a scalp and a chest so that a motion is very restricted during the measurement. In contrast, PPG is measured using one sensor which is attached to a body terminal part such as a finger, an earlobe, or a toe, so that it is possible to secure the motion of the user as compared with the ECG or EEG. However, due to a noise of a measurement environment and a motion of the user, the signal may be easily distorted. Therefore, a process of detecting whether such a noise is included at the time of signal processing and removing the noise is required.

SUMMARY

The present invention has been made to overcome the above-described problem of the related art and an object of the present disclosure is to provide a method for determining whether a motion artifact is included in a PPG signal which is one of bio-signals by receiving multiple signals and performing time-synchronization and removing the motion artifact.

One aspect of the present invention provides a motion artifact detecting method using wavelet transform which is capable of removing the problem caused by a radio noise and a motion artifact generated during the measurement of a PPG signal which is one of bio-signals, the method including: measuring a PPG signal; generating a signal obtained by removing a radio noise from the measured PPG signal; setting a reference signal from the signal from which the radio noise is removed; selecting a base signal based on the set reference signal; performing wavelet transform using the base signal; and detecting and removing a motion artifact using the wavelet-transformed value.

According to the motion artifact detecting method using wavelet transform according to the present disclosure configured as described above, it is possible to effectively detect whether a motion artifact is included in a PPG signal which is one of bio-signals to remove the motion artifact.

METHOD FOR CARRYING OUT THE INVENTION

It should be noted that technical terminologies used in the present invention are used to describe a specific exemplary embodiment but are not intended to limit the present invention. Further, the technical terminologies which are used in the present invention should be interpreted to have meanings that are generally understood by those with ordinary skill in the art to which the present invention pertains, unless specifically defined to have different meanings in the present invention, but not be interpreted as an excessively comprehensive meaning or an excessively restricted meaning.

Further, if a technical terminology used in the present invention is an incorrect technical terminology which does not precisely describe the spirit of the present invention, the technical terminology should be replaced with and understood as a technical terminology which may be correctly understood by those skilled in the art. Further, a general terminology used in the present invention should be interpreted as defined in a dictionary or in accordance with the context, but not be interpreted as an excessively restricted meaning.

Hereinafter, exemplary embodiments according to the present disclosure will be described in detail with reference to the accompanying drawings, and the same or similar components are denoted by the same reference numerals regardless of reference numerals, and repeated description thereof will be omitted.

In describing the present disclosure, when it is determined that a detailed description of a related publicly known technology may obscure the gist of the present disclosure, the detailed description thereof will be omitted. Further, it is noted that the accompanying drawings are used just for easily appreciating the spirit of the present disclosure and it should not be interpreted that the spirit of the present disclosure is limited by the accompanying drawings.

Figure 1:
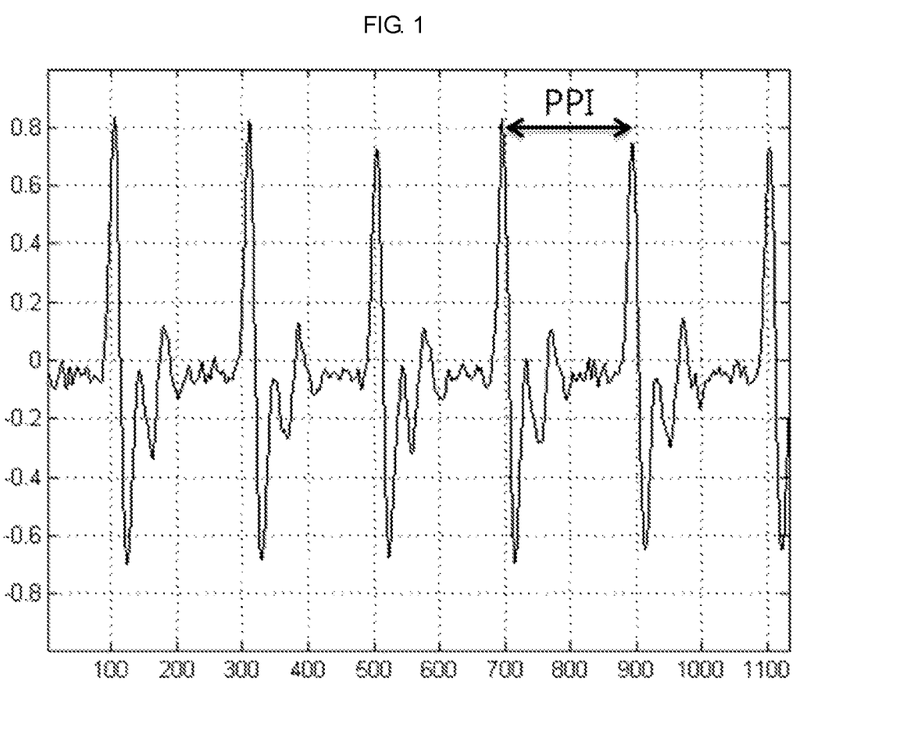
FIG. 1 is a signal graph illustrating a PPG signal detected by a PPG sensor.

FIG. 1 is a signal graph illustrating a PPG signal detected by a PPG sensor. Generally, a value used to detect a heartrate and a period thereof using a period of a PPG signal is a peak to peak interval (PPI) which means a time interval between a maximum value of one periodic signal and a maximum value of a next periodic signal. Therefore, the heartrate may be identified using the PPI of the PPG signal.

Generally, people have a heartrate of approximately 70 per minute, but the heartrate may vary by physical activity or external stimulus. When a body is tensed due to an external stimulus, the heartrate is increased and the PPI is decreased and when the body is relaxed, the heartrate is decreased and the PPI is increased. Such changes in the PPI may be used to determine a psychological state of a measurer or to determine the presence of a disease.

Figure 2:
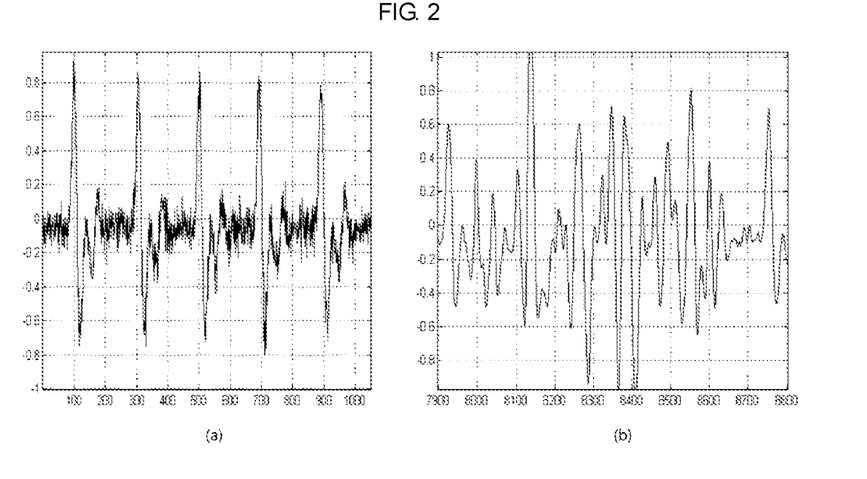
FIG. 2 is a signal graph illustrating a PPG signal in which a radio noise and a motion artifact are included.

FIG. 2 is a signal graph illustrating a PPG signal in which a radio noise and a motion artifact are included. When a radio noise is included in the PPG signal, the signal distortion may be generated as illustrated in FIG. 2A. Even though the radio noise does not significantly change the signal, the radio noise needs to be removed because when the PPI is detected, the radio noise serves as an obstacle. A normal PPG signal is activated in a frequency band of 0 to 4 Hz, but the radio noise is activated in a higher frequency band, so that the radio noise may be removed using a low pass filter.

When a motion artifact is included in the PPG signal, a serious distortion is generated as illustrated in FIG. 2B so that an original shape of the signal cannot be recognized. Such a motion artifact is generated in various frequency bands and affects a frequency band of 0 to 4 Hz in which the PPG signal is activated. Therefore, the motion artifact cannot be removed by a simple filter. The motion artifact serves as a serious obstacle when one period of a signal is detected, so that a signal processing technique for removing the motion artifact is required.

Figure 3:
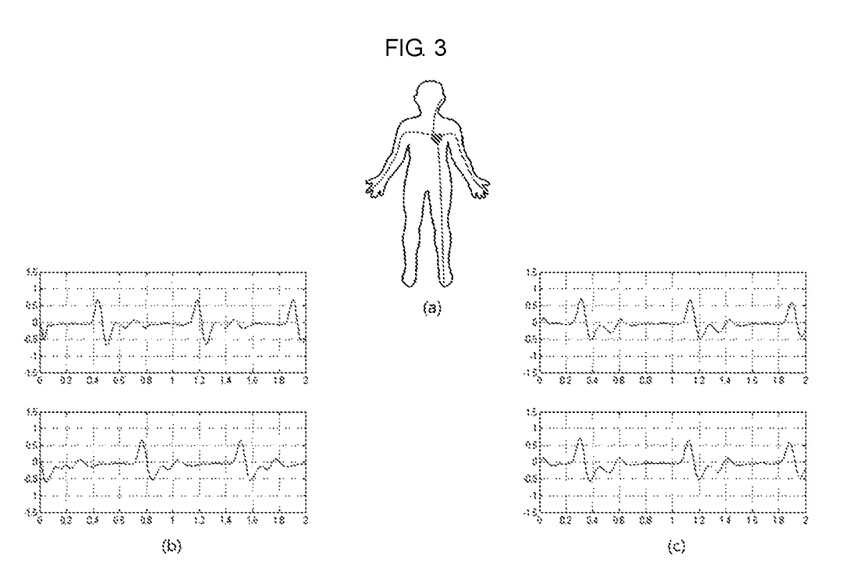
FIG. 3 is a graph illustrating a signal which is time-synchronized and a signal which is not time-synchronized according to the present invention.

FIG. 3 is a graph illustrating a signal which is time-synchronized and a signal which is not time-synchronized according to the present invention. Prior to removal of the motion noise using a signal received through multichannel, in a multi-measured signal, there may be differences in a measurement time and a signal magnitude due to a distance difference between a measurement position of each signal and the heart. FIG. 3B illustrates two signals which are not time-synchronized and FIG. 3C illustrates two signals which are time-synchronized.

The difference in the measurement time is represented as a difference in phases during a process of replacing a signal including the motion artifact with a normal signal thereafter. Therefore, it is desirable to correct the time difference between channels for effective signal processing. Further, it is desirable to correct a magnitude of a measured signal to adopt a signal optimized by analyzing multiple signals at the same time during the motion artifact removing process.

In order to correct the magnitude of the measured signal, a magnitude of a reference signal of a signal measured at each position is measured to set the reference signal to have the same magnitude of a signal having the largest magnitude. In order to correct the time difference of multi-received signals, a cross-correlation technique is applied to calculate the time difference of two signals and correct the time difference by shifting the signal as much as the calculated time difference.

Two arbitrary signals are assumed to describe a correcting method. A distance between a first receiving unit and the heart is different from a distance between a second receiving unit and the heart. Therefore, the time difference is caused by the distance difference. During the process of replacing a signal in which the motion artifact is generated with a normal signal, there may be a problem in that phases of two signals do not match due to the time difference of two signals. Therefore, in order to solve the above-described problem, the time difference of two signals needs to be corrected. The time difference of two signals is calculated using the following Equation 1 to which the cross-correlation technique is applied.

$$\hat{R}_{xy}(m) = \begin{cases} \sum_{n=0}^{N-m-1} x(n+m)y^*(n) & (m \geq 0) \\ \hat{R}_{yx}^*(-m) & (m < 0) \end{cases} \quad \text{(Equation 1)}$$

x: Signal of first measurement part
y: Signal of second measurement part

Here, $R_{xy}$ is a result obtained by applying a cross-correlation technique to a signal x of a first measurement part and a signal y of a second measurement part. When it is assumed that the signal x and the signal y are data having a length N, $R_{xy}$ is data having a length of $-(N-1)$ to $(N-1)$. m-th data of $R_{xy}$ is calculated depending on a sign in different ways. When m is positive, m-th data of $R_{xy}$ is calculated by $$\sum_{n=0}^{N-m-1} x(n+m)y^*(n)$$

and when m is negative, time is inversed from the data obtained when m is positive.

Figure 4:
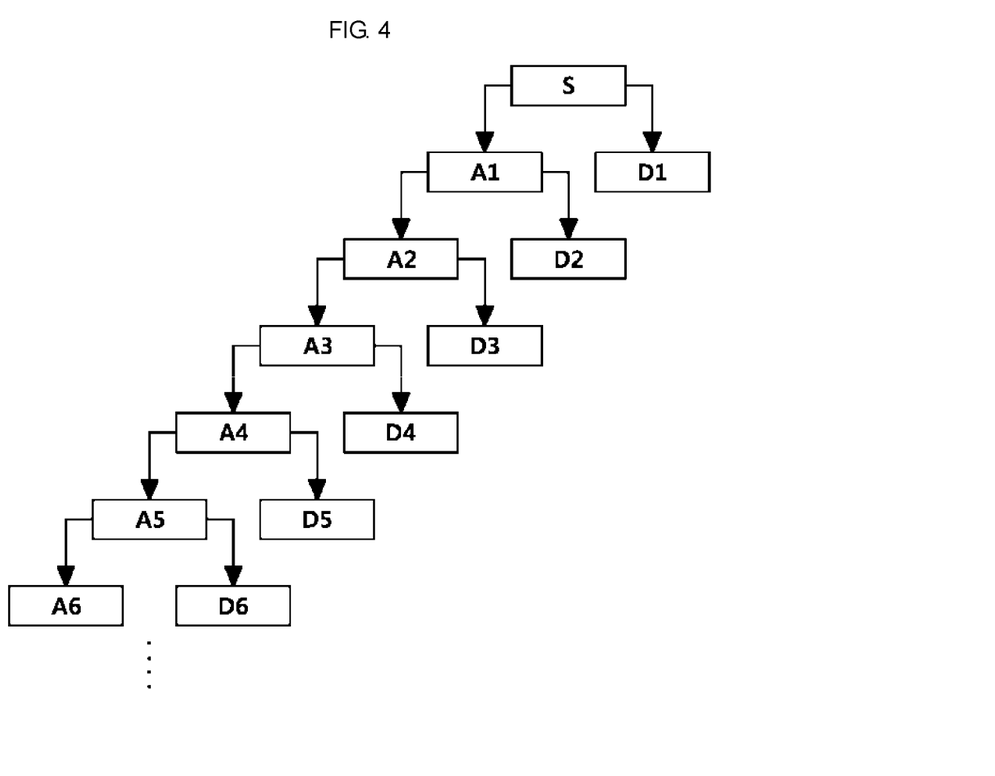
FIG. 4 is a view illustrating a process of wavelet transform of an original signal to decompose the signal according to the present invention.

FIG. 4 is a view illustrating a process of wavelet transform of an original signal to decompose the signal according to the present invention. In the discrete wavelet transform, the original signal S is represented by a sum of a signal which has passed through a low pass filter and a signal which has passed through a high pass filter. After the original signal passes through the low pass filter and the high pass filter, detail coefficients D[n] are output from the high pass filter and approximation coefficients A[n] are output from the low pass filter. Each output has a frequency band which is half the frequency band of the original signal. The original signal is represented by a sum of divided detail coefficients and approximation coefficients and also represented by the following equation.

$$S[n]=A[n]+D[n] \quad \text{(Equation 2)}$$

Whenever the wavelet transform is performed, the frequency band is divided into two bands and a low frequency band component is A[n] and a high frequency band component is D[n].

As described above when the wavelet transform is repeatedly performed on the signal A[n] which has passed through the low pass filter, the signal is divided as illustrated in FIG. 4 and a signal obtained after performing sixth wavelet transform may be represented by the following equation.

$$S=D1+D2+D3+D4+D5+D6+A6 \quad \text{(Equation 3)}$$

Figure 5:
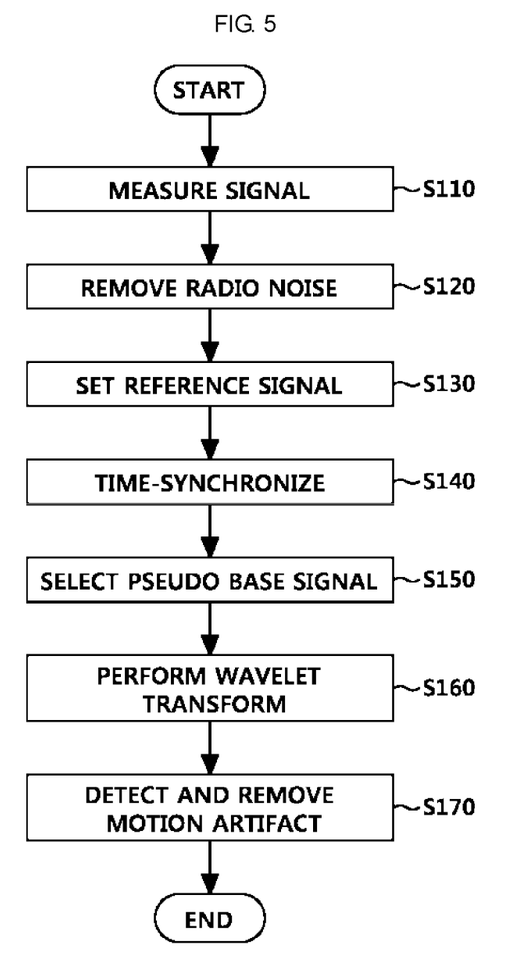
FIG. 5 is a flowchart illustrating steps of a method for detecting whether a motion artifact is included in the PPG signal and removing the motion artifact, according to the present invention.

FIG. 5 is a flowchart illustrating steps of a method for detecting whether a motion artifact is included in the PPG signal and removing the motion artifact, according to the present invention. As illustrated in FIG. 5, a method for detecting whether a motion artifact is included in a PPG signal and removing the motion artifact according to the present invention includes a step S110 of measuring a PPG signal through a multichannel, a step S120 of removing a signal noise of a radio band from the PPG signal, a step S130 of setting a reference signal, a step S140 of correcting and synchronizing a time difference between multiplexed signals by applying a cross-correlation technique in order to remove the motion artifact from the multichannel PPG signal based on the set reference signal, a step S150 of selecting a pseudo base signal, a step S160 of performing wavelet transform using a base signal, and a step S170 of detecting and removing the motion artifact using the transformed value.

First, a PPG signal is measured while a user does not move in a stable state for a predetermined time (S110). In the exemplary embodiment of the present invention, the signal is measured from the hand and the foot corresponding to a body terminal portion, but is not limited thereto. Further, in order to effectively remove the noise included in the signal thereafter, signals are measured from two or more parts of both hands and both feet.

When a body terminal part where the signal is measured is determined, if the user has a disease which may affect blood flow changes such as cold finger and toe syndrome, it is desirable to select a part having the smallest influence of the disease to measure a signal.

In order to set a precise reference signal, at the beginning of the signal measurement, the signal is measured while the user does not move in a stable state for a predetermined time. Since a base signal to be used for the subsequent wavelet transform is determined using the signal measured at this time, the signal is measured in an environment where the noise is not included as much as possible.

Even though the signal is measured in the environment where the noise is not included, a signal noise of a radio band due to mechanical and physical properties is included in the PPG signal measured in the PPG signal measuring step S110. The signal noise of the radio band serves as an obstacle to detect a period of the PPG signal, so that the radio noise needs to be removed using the low pass filter. Thereafter, when the wavelet transform is performed, a finite impulse response (FIR) based fast wavelet transform (FWT), that is, discrete wavelet transform is used, so that the radio noise is removed using an appropriate FIR filter.

Various filters such as a moving average filter, a Bartlet filter, a Hanning filter, and a Hamming filter may be used as the FIR filter and in the present invention, the Hamming filter having the largest minimum stop band attenuation is used, but the present invention is not limited thereto. In the exemplary embodiment of the present invention, a cutoff frequency is set to be 6 Hz, but is not limited thereto.

Next, a reference signal is set (S130) to set a base signal to be used for wavelet transform from a signal from which the radio noise is removed. The reference signal needs to be measured in a stable state of the user and may be measured without movement. Even though the signal is measured under the above condition, due to a characteristic of the sensor, at the beginning, a signal which is smaller than a magnitude of a normal pulse wave of the user is detected and an amplitude and a magnitude are not even. Therefore, since a signal at the beginning of the measurement cannot be used as a reference signal, the reference signal is set using a normal signal after a predetermined time is elapsed.

In this case, since a period of a normal PPG signal is 0.6 to 1.2 seconds, a first period after three seconds which correspond to approximately three periods is set as a reference signal. The PPG signals have different characteristics and shapes for every people and also have different shapes depending on measurement parts. Since the reference signal is selected by reflecting a pulse wave characteristic of each user and a wavelet transform base signal is determined based on the reference signal, it is easy to detect the motion artifacts.

In the signal multi-measured in step S110, the measurement time and the magnitude may vary due to a distance difference between the measurement positions of each signal and the heart. The difference in the measurement time is represented as a difference in phases during a process of replacing a signal including the motion artifact with a normal signal thereafter. Therefore, the time difference and the magnitude difference between channels are corrected for effective signal processing (S140).

In order to correct the time difference of multi-received signals, a cross-correlation technique is applied to calculate the time difference of two signals and correct the time difference by shifting the signal as much as the calculated time difference.

Further, during the process of detecting and removing the motion artifacts, the magnitude of the measured signal is also corrected to analyze multi-signal for the same time and choose an optimized signal. In order to correct the magnitude of the measured signal, a magnitude of a reference signal of a signal measured at each position is measured to set the measured signal to have the same magnitude as a signal having the largest magnitude.

Next, a pseudo base signal to be used for wavelet transform is selected (S150) using the reference signal of the user set in step S130. In this case, as the base signal, the closest function among various base functions is chosen using the base signal of the user, the base function, and the cross-correlation technique. There is a scaling function among various base functions used for the wavelet transform. Further, an FIR filter may be applied to be suitable for FWT. 'Harr(harr)', 'Daubechies (dbN)', 'Symlets (symN)', 'Coiflets (coifN)', 'Biothogonal wavelets (biorN)', 'Reverse biothogonal wavelets (rbioN)', 'Discrete approximation of Meyer wavelet (dmey)' which are base functions in which discrete wavelet transform is allowed are adopted to compare the base functions and the reference signal using the cross-correlation technique.

A base function which is the closest to the reference signal among the compared base functions is set as a general function of wavelet transform to be used later. When the base function which is the closest to the reference signal is selected, numerical values of the maximum value of the cross-correlation technique are compared by applying the cross-correlation technique to the base function and the reference signal to select the largest value as a base signal.

To quantify a similar degree, the cross-correlation function of matlab is used to find the result value of the cross-correlation technique and the largest value is found using a max function and then the maximum value among values corresponding to maximum values of the base signals is measured again, to determine the base signal.

Next, the wavelet transform is performed (S160) using the base function set in step S150. Whenever one wavelet transform is performed, the signal is divided into an approximation A[n] part and a detail D[n] part. A[n] represents a low frequency band and D[n] represents a high frequency band. In this case, the wavelet transform is repeated so that the frequency band of A[n] is 0 to 4 Hz. The reason for this repetition is that a normal heartbeat is less than 4 Hz. In order to easily detect one period, a transform step is set to include a period shorter than 4 Hz. Generally, a transform step is determined using a sampling frequency and a method for determining the number of times of wavelet transform will be described with reference to FIG. 6.

Figure 6:
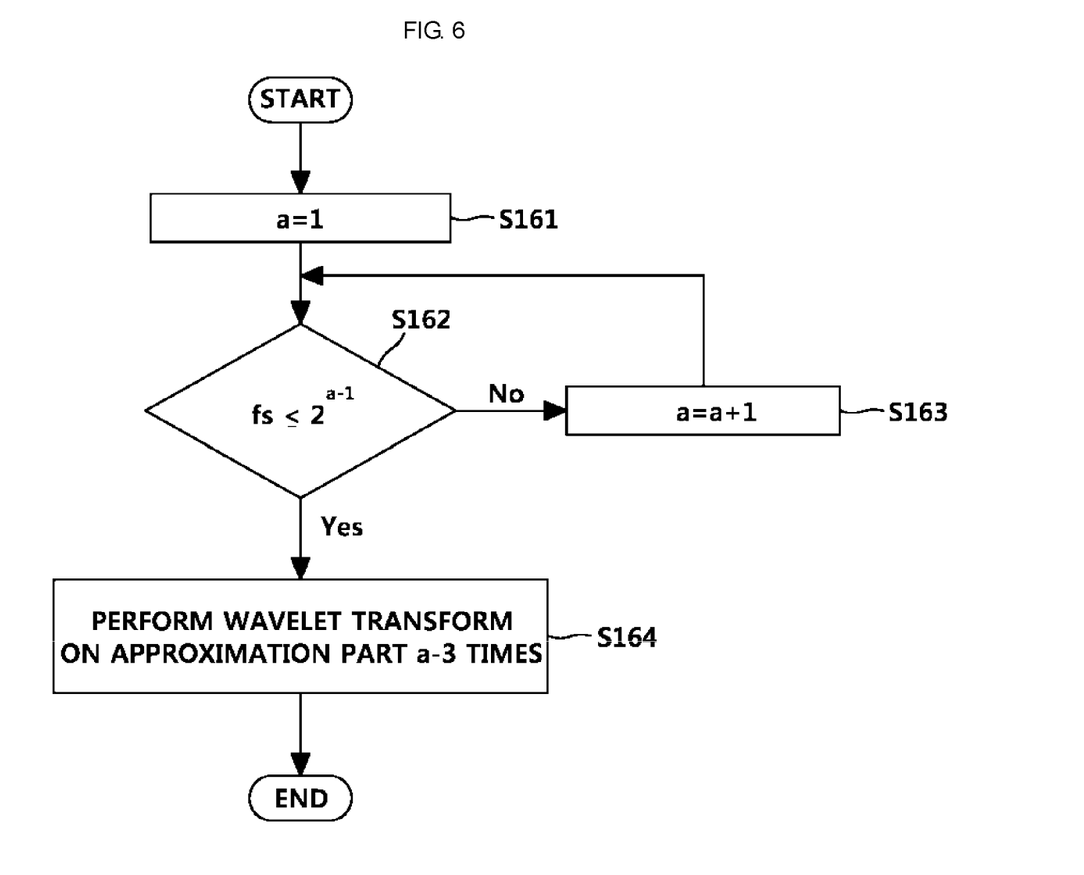
FIG. 6 is a flowchart illustrating a step of determining the number of times of wavelet transform according to the present invention.

FIG. 6 is a flowchart illustrating a step of determining the number of times of wavelet transform according to the present invention. An initial value of a is 1 (S161) and it is determined whether to satisfy a relationship of fs≤2^(a−1) in step S162. When the relationship is not satisfied, 1 is added to the value of a (S163) to repeat the step S162.

fs is a sampling frequency and the smallest a−3 satisfying the relationship of fs≤2^(a−1) is the number of times of transform to be repeated. A[n] is wavelet-transformed as many as the smallest number of times a−3 which satisfies the relationship of fs≤2^(a−1) (S164). The radio region and a low frequency region are divided by the wavelet transform so that A[n] and D[n] are divided by a relative criterion.

In the exemplary embodiment of the present invention, the wavelet transform is performed on A[n], but is not limited thereto. Depending on which part is transformed, the values of A[n] and D[n] may vary. In the wavelet transform, not only the A[n] may be consistently divided and but also D[n] may be set as a transform target to be divided.

Specifically, in order to obtain a desired band, at the time of one-time division, it is determined that which signal of A[n] and D[n] is selected to be divided. For example, in order to obtain a signal in a frequency band of 32 to 48, the frequency is divided to be 0 to 128 and 128 to 256 by one transform, (0-64), (64-128), and (128-256) (A[n] transform) by two transforms, (0-32), (32-64), (64-128), and (128-256) (A[n] transform) by three transforms, and (0-32), (32-48), (48-64), (64-128), and (128-256) (D[n] transform) by four transforms. Therefore, a desired frequency band signal may be obtained. As described above, whenever one wavelet transform is performed, it is possible to select a signal to be divided and whenever the wavelet transform is performed, the signal is divided into A[n] and D[n].

Since the sampling frequency of the signal used in the exemplary embodiment of the present invention is 256 Hz, A[n] which is sixth-transformed includes the section of 0 to 4 Hz. Table 1 represents a frequency distribution of a signal which is wavelet-transformed by the method of FIG. 3.

TABLE 1

| n    | 1       | 2      | 3     | 4     | 5    | 6   |
|------|---------|--------|-------|-------|------|-----|
| A[n] | 0-128   | 0-64   | 0-32  | 0-16  | 0-8  | 0-4 |
| D[n] | 128-256 | 64-128 | 32-64 | 16-32 | 8-16 | 4-8 |

As represented in Equation 2, it is understood that a total of D[1]+D[2]+D[3]+D[4]+D[5]+D[6]+A[6] becomes an original sampling frequency signal.

Next, one period of a pulse wave of the user is detected using a period when a heartbeat is activated and it is identified whether the motion artifact is included in the detected signal using the period and the motion artifact is removed (S170). A method for determining whether the motion artifact is included is illustrated in FIG. 7.

Figure 7:
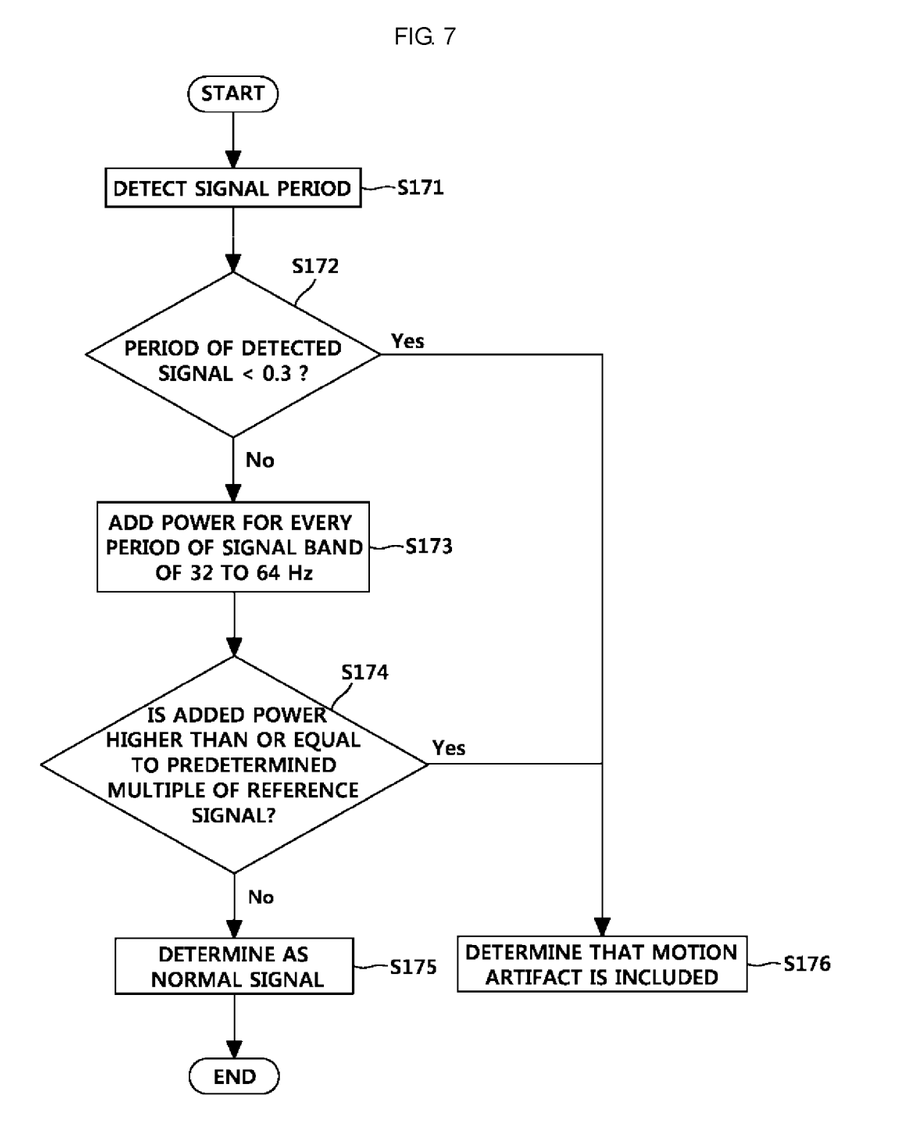
FIG. 7 is a flowchart illustrating steps of a method for determining a motion artifact according to the present invention.

FIG. 7 is a flowchart illustrating steps of a method for determining a motion artifact according to the present invention. When one period is detected using the period when the heartbeat is activated, the signal period is detected using the PPI of the signal (S171).

When the motion artifact is not included, the PPI is represented at a regular interval but the motion artifact is included, the PPI is changed. A normal heartbeat is approximately 0.8 seconds and the period when the motion artifact is generated is 0.3 to 1.6 seconds, which is rapidly changed. Therefore, it is determined whether the period is shorter than 0.3 seconds (S172). If the period is shorter than 0.3 seconds, it is determined that the motion artifact is included (S176). A period which becomes a determination criterion in step S172 is set to be 0.3 seconds, but may vary depending on the situation.

When the motion artifact is determined, even though there is an influence by the heartbeat, a frequency band in which the influence of the heartbeat is insignificant as compared with other frequency band and the influence of the motion artifact is large as compared with the heart rate is used. A portion corresponding to the above frequency band is approximately 32 to 64 Hz. An average period of heartbeat is approximately 0.8 seconds. When a component value of the frequency band is large, it is determined that the motion artifact is included in the signal.

When the motion artifact is determined, after adding powers of signals of respective periods and signals in a frequency band of 32 to 64 Hz of the reference signal (S173), the powers are compared to determine whether the signals of respective periods are higher than or equal to a predetermined multiple of the reference signal (S174). When the power of the signal is higher than or equal to a predetermined multiple of the reference signal, it is determined that the motion artifact is included in the period (S176) and when the power of the signal is lower than the predetermined multiple of the reference signal, it is determined that the signal is a normal signal (S175). During the process of determining whether the power is a predetermined multiple or higher of the reference signal, the multiple may be set to be 1.4 to 1.6, and desirably 1.5.

When in step S176, it is determined that the motion artifact is included in the multi-received signals, the motion artifact is removed using a selective combining technique. The selective combining technique is a method of outputting an ideal signal by outputting the best signal for every section among signals obtained from each channel.

The motion artifact is determined for every period of the multi-receive signal. When one or more signals are normal signals in which the motion artifact is not included, a signal having the largest magnitude among the normal signals is output. When all signals include motion artifacts, a signal with the smallest influence of the motion artifact among all the signals is output.

In order to compare the degrees of influence of the motion artifacts of respect periods, an SNS of each signal is calculated using Equation 4. The SNS is calculated using a signal in the frequency band of 32 to 64 Hz which is used to determine whether the motion artifact is included and a signal having a value of SNS which is the closest to 1 is a signal having the smallest influence of the motion artifact. The motion artifact of the signal may be effectively removed using the SNS and the selective combining technique.

$$SNS = \text{power of signal and noise/power of reference signal} \quad \text{(Equation 4)}$$

Figure 8:
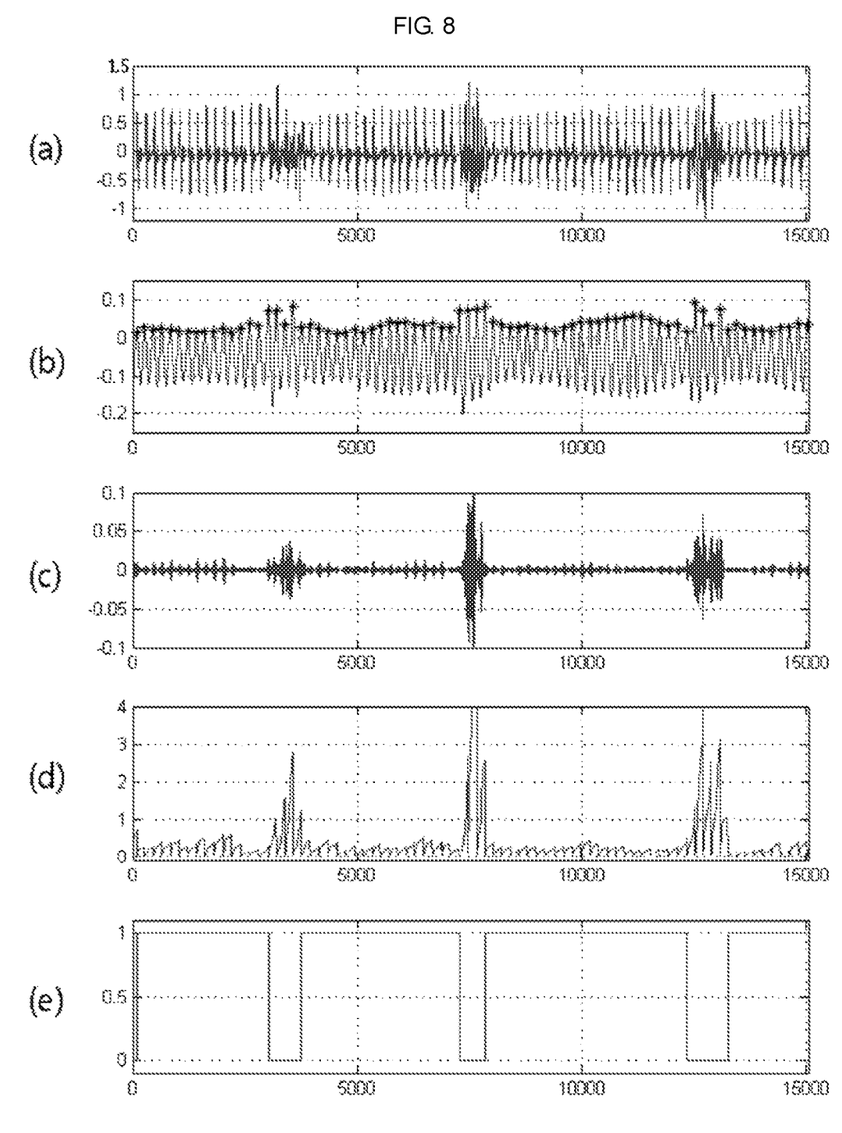
FIG. 8 is a graph illustrating a motion artifact detecting result according to the present invention.

FIG. 8 is a graph illustrating a motion artifact detecting result according to the present invention. The PPG signal which generates the motion artifact is identified from three parts in which the PPI is short in FIG. 8A. After setting the reference signal to determine the motion artifact and setting the base function, the wavelet transform is performed to represent an A[n] period having a frequency range of 0 to 4 Hz and a D[n] period having a frequency range of 32 to 64 Hz. A period when the power of each period of the D[n] period is 1.5 times or higher than the power of the corresponding period of the reference signal is determined as a period where the motion artifact is generated.

Since the reference signal is set by a signal at the beginning of the signal measurement, an amplitude of the reference signal is not sufficiently broader, and even though the user is not moving, there may be a change in heartbeat due to psychological reasons such as change of emotions or tension. Therefore, it is desirable to set a sufficient error range to be 1.5 times.

As a result of actual experiment, when the motion artifact is determined based on 1.2 times, not only the motion artifact, but also the normal signal is determined as a motion artifact. Further, when the motion artifact is determined based on 1.7 times, the motion artifact is not normally distinguished. Therefore, the experiment is performed based on 1.5 times which is the most appropriate.

FIG. 8B illustrates a result of adding powers of a section of 0 to 4 Hz from the beginning of one period to the next period, FIG. 8C illustrates a result of adding powers of a section of 32 to 64 Hz, and FIG. 8D illustrates a result of adding the powers of a section of 32 to 64 Hz. As illustrated in FIG. 8C, it is understood that in the case of a normal pulse wave, the power of D[n] is very low and when the motion artifact is included, the power is high.

The period of each signal is determined from FIG. 8B and a magnitude of the signal for each period is calculated as illustrated in FIG. 8D and then the magnitude of the signal is compared with the magnitude of the reference signal to calculate how much the motion artifact is included (SNS). As illustrated in FIG. 8E, when it is determined that the motion artifact is actually included, 0 is output during the period and when it is determined that the motion artifact is not included, 1 is output during the period. Therefore, it is identified that when the motion artifact is included, it is precisely determined. A result of determining whether the motion artifact is included for every period after calculating and comparing the SNS for each channel and selecting a signal in which small amount of motion artifact is included for every period is illustrated in FIG. 9.

Figure 9:
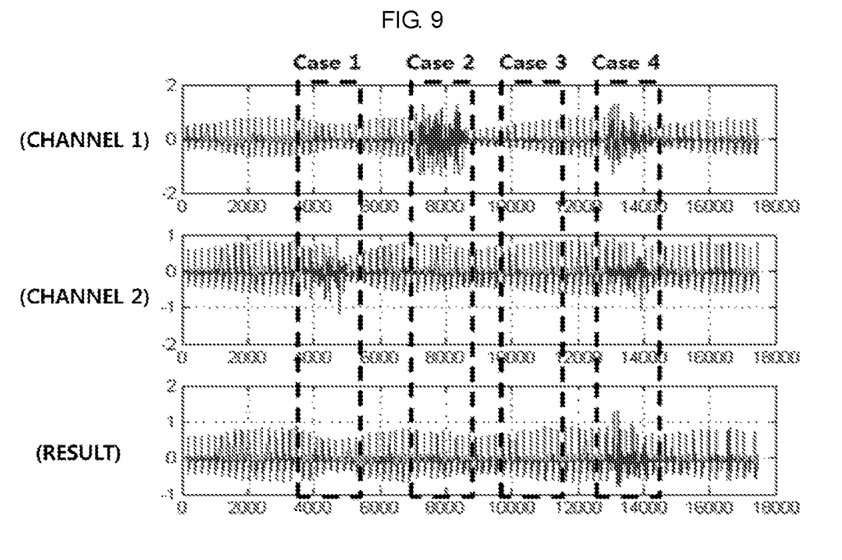
FIG. 9 is a graph illustrating a motion artifact removing result according to the present invention.

FIG. 9 is a graph illustrating a motion artifact removing result according to the present invention. In Case 1 and Case 2 of FIG. 9, the motion artifact is generated in one signal, in Case 3, both signals do not include the motion artifacts, and in Case 4, both signals include the motion artifacts. When the motion artifact is included in one signal, a period where the motion artifact is not included is output. When both signals do not include the motion artifacts, a signal having a larger magnitude between two signals is output. When both signals include the motion artifacts, the SNS is calculated to output a signal having a less influence of the motion artifact between two signals.

In FIG. 9, in channel 1, it is determined whether a signal in which a motion artifact is included for 20% of time includes a motion artifact using wavelet transform. In channel 2, it is determined whether a signal in which a motion artifact is included for 15% of time includes a motion artifact using wavelet transform. In channel 1, it is precisely determined that the motion artifact is included for 19.4% of time and 14.9% of time and as a result of removing the motion artifact based thereon, a ratio of the motion artifact with respect to the entire signal is improved to 4.29%.

As represented in Table 2, as a result of experiment by varying a degree of included noise, it is confirmed that the influence of the noise on the signal is reduced.

TABLE 2

| | | Channel 1 | | Channel 2 | | Selected signal | |
|---|---|---|---|---|---|---|---|
| | | Noise(%) | Detected noise(%) | Noise(%) | Detected noise(%) | Noise(%) | |
| A | Hand | 20 | 19.4 | Hand 15 | 14.9 | 4.29 | 78.55 |
| | Hand | 20 | 19.12 | Hand 10 | 11.2 | 7.33 | 63.35 |
| | Hand | 30 | 29.78 | Hand 30 | 29.77 | 5.18 | 82.73 |
| | Hand | 20 | 18.35 | Foot 15 | 14.69 | 2.89 | 85.55 |
| B | Hand | 20 | 20.39 | Hand 15 | 14.44 | 5.18 | 74.10 |
| | Hand | 20 | 20.33 | Hand 10 | 9.56 | 5.34 | 73.30 |
| | Hand | 30 | 30.61 | Hand 30 | 29.34 | 4.59 | 84.70 |
| | Hand | 20 | 19.65 | Foot 15 | 16.12 | 3.78 | 81.10 |
| C | Hand | 20 | 19.87 | Hand 15 | 16.31 | 7.52 | 62.40 |
| | Hand | 20 | 18.63 | Hand 10 | 11.26 | 4.26 | 78.70 |
| | Hand | 30 | 28.65 | Hand 30 | 31.09 | 9.43 | 68.57 |
| | Hand | 20 | 20.83 | Foot 15 | 14.69 | 6.25 | 68.75 |
| D | Hand | 20 | 21.13 | Hand 15 | 15.68 | 6.24 | 68.80 |
| | Hand | 20 | 20.96 | Hand 10 | 9.86 | 6.69 | 66.55 |
| | Hand | 30 | 30.42 | Hand 30 | 28.96 | 8.37 | 72.10 |
| | Hand | 20 | 19.58 | Foot 15 | 14.76 | 4.75 | 76.25 |

The features, structures, effects, and the like described in the foregoing embodiments are included in at least one embodiment of the present invention and are not necessarily limited to one embodiment. Moreover, the features, structures, effects, and the like illustrated in each embodiment may be combined or modified by those skilled in the art for the other embodiments to be carried out.

Therefore, the combination and the modification of the present invention are interpreted to be included within the scope of the present invention. In the above description, the present invention has been described based on the exemplary embodiments, but the exemplary embodiments are for illustrative, and do not limit the present invention, and those skilled in the art will appreciate that various modifications and applications, which are not exemplified in the above description, may be made without departing from the scope of the essential characteristic of the present exemplary embodiments. For example, each component described in detail in the embodiment can be modified. Further, the differences related to the modification and the application should be construed as being included in the scope of the present invention defined in the accompanying claims.

What is claimed is:

1. A motion artifact detecting method using wavelet transform, comprising:
   measuring a Photoplethysmography (PPG) signal through a multichannel;
   generating a signal obtained by removing a radio noise from the measured PPG signal;
   setting a reference signal from the signal from which the radio noise is removed, the reference signal being set at a first period after a predetermined time elapses;
   selecting a base signal based on the set reference signal and a plurality of base functions which can be wavelet-transformed;
   performing wavelet transform using the base signal; and
   detecting and removing a motion artifact using the wavelet-transformed value,
   the detecting a motion artifact further comprising,
   detecting a signal period when a heartbeat is activated;
   determining whether the signal period is shorter than a criterion period preset based on a change of peak to peak interval (PPI);
   if the signal period is shorter than the criterion period, determining that the motion artifact is included; and
   if the signal period is not shorter than the criterion period, determining that the motion artifact is included when a value obtained by adding powers for respective periods of a predetermined frequency band is a predetermined multiple or higher of a power of the reference signal.

2. The motion artifact detecting method of claim 1, wherein in the generating of a signal from which the radio noise is removed, a low pass filter is used.

3. The motion artifact detecting method of claim 1, wherein during the selecting of a base signal, maximum values of a cross-correlation technique are compared by applying the cross-correlation technique to the plurality of base functions and the reference signal to select the largest value as a base signal.

4. The motion artifact detecting method of claim 1, wherein during the performing of wavelet transform using a base signal, the wavelet transform is repeated such that the frequency of a low frequency band has a frequency band of 0 to 4 Hz.

5. The motion artifact detecting method of claim 1, further comprising:
   after the setting of a reference signal, correcting a difference between multiplexed signals by applying the cross-correlation technique to remove the motion artifact from the multichannel PPG signal based on the reference signal.

6. The motion artifact detecting method of claim 5, wherein during the correcting the difference between signals, at least one of a time difference and a magnitude of the PPG signal measured through the multichannel is corrected.

* * * * *